United States Patent
Modrusan

(10) Patent No.: US 7,122,314 B2
(45) Date of Patent: Oct. 17, 2006

(54) METHODS FOR DETECTING VANCOMYCIN-RESISTANT MICROORGANISMS AND COMPOSITIONS THEREFOR

(75) Inventor: Zora D Modrusan, Fremont, CA (US)

(73) Assignee: ID Biomedical Corporation, Vancouver (CA)

( * ) Notice: Subject to any disclaimer, the term of this patent is extended or adjusted under 35 U.S.C. 154(b) by 488 days.

(21) Appl. No.: 10/357,314

(22) Filed: Jan. 30, 2003

(65) Prior Publication Data

US 2004/0096937 A1    May 20, 2004

Related U.S. Application Data

(60) Provisional application No. 60/352,750, filed on Jan. 30, 2002.

(51) Int. Cl.
*C12Q 1/68*    (2006.01)
*C12Q 1/14*    (2006.01)
*C12Q 1/10*    (2006.01)

(52) U.S. Cl. ............... 435/6; 435/36; 435/38
(58) Field of Classification Search .......... 435/6, 435/36, 38; 536/23.1
See application file for complete search history.

(56) References Cited

U.S. PATENT DOCUMENTS

| | | | |
|---|---|---|---|
| 4,847,194 A | 7/1989 | Quante | 435/7 |
| 4,855,240 A | 8/1989 | Rosenstein et al. | 436/514 |
| 4,861,728 A | 8/1989 | Wagner | 436/501 |
| 4,865,997 A | 9/1989 | Stoker | 436/541 |
| 4,874,710 A | 10/1989 | Piran | 435/518 |
| 4,876,187 A | 10/1989 | Duck et al. | 435/6 |
| 4,904,583 A | 2/1990 | Mapes et al. | 435/7 |
| 4,920,046 A | 4/1990 | McFarland et al. | 435/7 |
| 4,962,024 A | 10/1990 | Schulte | 435/14 |
| 5,011,769 A | 4/1991 | Duck et al. | 435/6 |
| 5,073,340 A | 12/1991 | Covington et al. | 422/56 |
| 5,093,231 A | 3/1992 | Hoke | 435/5 |
| 5,130,238 A | 7/1992 | Malek et al. | 435/91 |
| 5,135,847 A | 8/1992 | Hoke | 435/5 |
| 5,139,934 A | 8/1992 | Stewart et al. | 435/7.92 |
| 5,166,054 A | 11/1992 | Naqui | 435/7.91 |
| 5,169,766 A | 12/1992 | Schuster et al. | 435/91 |
| 5,188,937 A | 2/1993 | Schulte et al. | 435/7.36 |
| 5,194,370 A | 3/1993 | Berninger et al. | 435/6 |
| 5,204,061 A | 4/1993 | Covington et al. | 422/56 |
| 5,208,143 A | 5/1993 | Henderson et al. | 435/5 |
| 5,210,015 A | 5/1993 | Gelfand et al. | 435/6 |
| 5,215,899 A | 6/1993 | Dattagupta | 435/6 |
| 5,260,025 A | 11/1993 | Covington et al. | 422/56 |
| 5,369,036 A | 11/1994 | Mercolino et al. | 436/523 |
| 5,399,491 A | 3/1995 | Kacian et al. | 435/91.21 |
| 5,399,500 A | 3/1995 | Oppenheimer et al. | 436/500 |
| 5,403,711 A | 4/1995 | Walder et al. | 435/6 |
| 5,409,818 A | 4/1995 | Davey et al. | 435/91.21 |
| 5,422,253 A | 6/1995 | Dahlberg et al. | 435/91.53 |
| 5,457,027 A | 10/1995 | Nadeau et al. | 435/6 |
| 5,474,916 A | 12/1995 | Reischl et al. | 435/91.2 |
| 5,480,784 A | 1/1996 | Kacian et al. | 435/91.21 |
| 5,487,972 A | 1/1996 | Gelfand et al. | 435/6 |
| 5,514,785 A | 5/1996 | Van Ness et al. | 536/22.1 |
| 5,547,861 A | 8/1996 | Nadeau et al. | 435/91.2 |
| 5,554,517 A | 9/1996 | Davey et al. | 435/91.21 |
| 5,578,270 A | 11/1996 | Reichler et al. | 422/67 |
| 5,589,332 A | 12/1996 | Shih et al. | 435/6 |
| 5,635,362 A | 6/1997 | Levine et al. | 435/7.24 |
| 5,639,428 A | 6/1997 | Cottingham | 422/112 |
| 5,656,430 A | 8/1997 | Chirikjian et al. | 435/6 |
| 5,660,988 A | 8/1997 | Duck et al. | 435/6 |
| 5,691,142 A | 11/1997 | Dahlberg et al. | 435/6 |
| 5,698,400 A | 12/1997 | Cotton et al. | 435/6 |
| 5,719,028 A | 2/1998 | Dahlberg et al. | 435/6 |
| 5,731,146 A | 3/1998 | Duck et al. | 435/6 |
| 5,747,255 A | 5/1998 | Brenner | 435/6 |
| 5,770,361 A | 6/1998 | Arthur et al. | 435/6 |
| 6,136,533 A | 10/2000 | Bekkaoui | 435/6 |
| 6,274,316 B1 | 8/2001 | Modrusan | 435/6 |
| 6,503,709 B1 | 1/2003 | Bekkaoui et al. | 435/6 |

FOREIGN PATENT DOCUMENTS

| | | |
|---|---|---|
| EP | 227 976 A2 | 7/1987 |
| EP | 229 701 B1 | 9/1995 |
| WO | WO 92/08800 | 5/1992 |
| WO | WO 92/22671 | 12/1992 |
| WO | WO 94/06913 * | 3/1994 |
| WO | WO 95/00667 | 1/1995 |
| WO | WO 95/05480 | 2/1995 |
| WO | WO 95/14106 | 5/1995 |
| WO | WO 96/02668 | 2/1996 |
| WO | WO 96/08582 | 3/1996 |
| WO | WO 96/21144 | 7/1996 |
| WO | WO 97/09444 | 3/1997 |
| WO | WO 97/19193 | 5/1997 |

(Continued)

OTHER PUBLICATIONS

Centinkaya etal. Vancomycin-Resistant Enterococci. Clinical Microbiology Reviews, vol. 13, No. 4, pp. 686-707, Oct. 2000.*

(Continued)

*Primary Examiner*—Kenneth R. Horlick
*Assistant Examiner*—Cynthia Wilder
(74) *Attorney, Agent, or Firm*—Seed IP Law Group PLLC

(57) ABSTRACT

A method for detecting the presence of a vancomycin-resistant microorganism in a biological sample using a single chimeric probe in a cycling probe reaction.

4 Claims, 2 Drawing Sheets

FOREIGN PATENT DOCUMENTS

WO      WO 99/01570      1/1999

OTHER PUBLICATIONS

Figure 1:
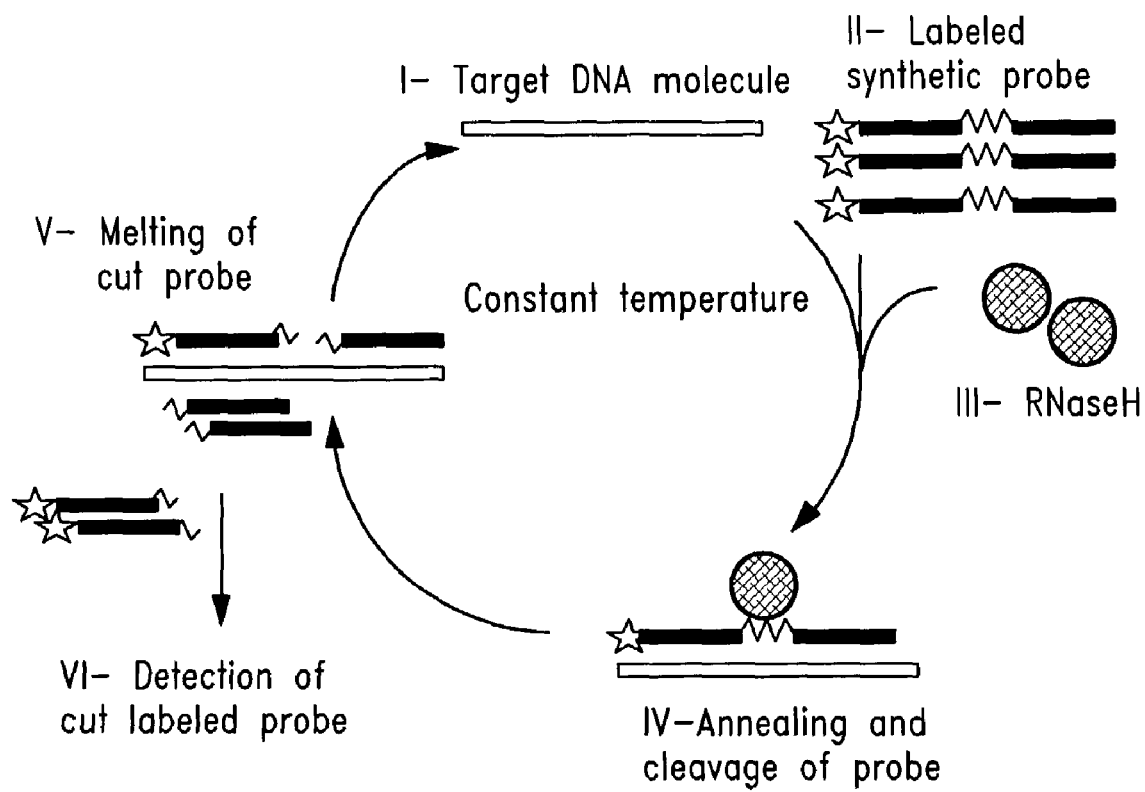

Lu et al., "High Prevalence of VanB2 Vancomycin-Resistant *Enterococcus faecium* in Taiwan," *Journal of Clinical Microbiology* 39(6):2140-2145, Jun. 2001.

Bekkaoui et al., "Cycling Probe Technology with RNase H Attached to an Oligonucleotide," *BioTechniques* 20(2):240-248, Feb. 1996.

Beggs et al., "Characterization of Mycobacterium Tuberculosis Complex Direct Repeat Sequence for Use in Cycling Probe Reaction," *Journal of Clinical Microbiology* 34(12): 2985-2989, 1996.

Patel et al., "Multiplex PCR detection of *vanA*, *vanB*, *vanC-1*, and *vanC-2/3* Genes in Enterococci," *Journal of Clinical Microbiology* 35(3): 703-707, 1997.

Gold et al., "A Gene Conferring Resistance to Vancomycin but Not Teicoplanin in Isolates of *Enterococcus faecalis* and *Enterococcus faecium* Demonstrates Homology with *vanB*, *vanA*, and *vanC* Genes of Enterococci," *Antimicrobial Agents and Chemotherapy* 37(8):1604-1609, Aug. 1993.

Power et al., "*vanA* genes in vancomycin-resistant clinical isolates of *Oerskovia turbata* and *Arcanobacterium* (*Corynebacterium*) *haemolyticum*," *Journal of Antimicrobial Chemotherapy* 36:595-606, 1995.

Poyart et al., "Emergence of Vancomycin Resistance in the Genus *Streptococcus*: Characterization of a *vanB* Transferable Determinant in *Streptococcus bovis*," *Antimicrobial Agents And Chemotherapy* 41:24-29, Jan. 1997.

Brisson-Noël et al., "Cloning and Heterospecific Expression of the Resistance Determinant *vanA* Encoding High-Level Resistance to Glycopeptides in *Enterococcus faecium* BM4147," *Antimicrobial Agents And Chemotherapy* 34(5): 924-927, 1990.

Dutka-Malen et al., "Sequence of the *vanC* gene of *Enterococcus gallinarum* BM4174 encoding a D-alanine:D-alanine ligase-related protein necessary for vancomycin resistance" *Gene* 112: 53-58, 1992.

Evers et al., "The *vanB* gene of vancomycin-resistant *Enterococcus faecali* V583 is structurally related to genes encoding D-Ala:D-Ala ligases and glycopeptide-resistance proteins VanA and VanC," *Gene* 124: 143-144, 1993.

Leclercq and Courvalin, "Resistance to Glycopeptides in Enterococci," *Clinical Infectious Diseases* 24(4):545-556, Apr. 1997.

Dutka-Malen et al., "Phenotypic and Genotypic Heterogeneity of Glycopeptide Resistance Determinants in Gram-Positive Bacteria," *Antimicrobial Agents And Chemotherapy* 34(10): 1875-1879, 1990.

Navarro and Courvalin, "Analysis of Genes Encoding D-Alanine-D-Alanine Ligase-Related Enzymes in *Enterococcus casseliflavus* and *Enterococcus flavescens*" *Antimicrobial Agents and Chemotherapy* 38(8): 1788-1793, Aug. 1994.

Aarestrup et al., "Glycopeptide Susceptibility among Danish *Enterococcus faecium* and *Enterococcus faecalis* Isolates of Animal and Human Origin and PCR Identification of Genes within the VanA Cluster," *Antimicrobial Agents and Chemotherapy* 40(8):1938-1940, Aug. 1996.

Dutka-Malen et al.1, "The VANA glycopeptide resistance protein is related to D-alanyl-D-alanine ligase cell wall biosynthesis enzymes," *Mol. Gen. Genet.* 224: 364-372, 1990.

Evers et al., "Sequence of the *vanB* and *ddl* genes encoding D-alanine: D-lactate and D-alanine: D-alanine ligases in vacomycin-resistant *enterococcus faecalis* V583," *Gene* 140:97-102, 1994.

Arthur et al., "The *vanZ* gene of Tn*1546* from *Enterococcus faecium* BM4147 confers resistance to teicoplanin," *Gene* 154: 87-92, 1995.

Al-Obeid et al., "Comparison of vancomycin-inducible proteins from four strains of *Enterocci*," *FEMS Microbiology Letters* 70: 101-106, 1990.

Bugg et al., "Identification of Vancomycin Resistance Protein VanA as a D-Alanine:D-Alanine Ligase of Altered Substrate Specificity," *Biochemistry* 30: 2017-2021, 1991.

Leclercq et al., "Transferable Vancomycin and Teicoplanin Resistance in *Enterococcus faecium*," *Antimicrobial Agents And Chemotherapy* 33(1): 10-15, 1989.

Sahm et al., "In Vitro Susceptibility Studies of Vancomycin-Resistant *Enterococcus faecalis*," *Antimicrobial Agents And Chemotherapy* 33(9): 1588-1591, 1989.

Kanaya and Itaya, "Expression, Purification, and Characterization of a Recombinant Ribonuclease H from *Thermus thermophilus* HB8," *The Journal of Biological Chemistry* 267(14):10184-10192, May 15, 1992.

Nielsen et al., "Sequence-Selective Recognition of DNA by Strand Displacement with a Thymine-Substituted Polyamide," *Science* 254(5037):1497-1500, Dec. 6, 1991.

Egholm et al., "PNA hybridizes to complementary oligonucleotides obeying the Watson-Crick hydrogen-bonding rules," *Nature* 365(*Issue No.* 6446):566-568, Oct. 7, 1993.

\* cited by examiner

METHODS FOR DETECTING VANCOMYCIN-RESISTANT MICROORGANISMS AND COMPOSITIONS THEREFOR

CROSS-REFERENCE TO RELATED APPLICATION

This application claims the benefit of U.S. Provisional Patent Application No. 60/352,750 filed Jan. 30, 2002, where this provisional application is incorporated herein by reference in its entirety.

BACKGROUND OF THE INVENTION

1. Field of the Invention

The present invention relates generally to probe sequences and methods for detecting target nucleic acid molecules, and more specifically, to a probe for detecting antibiotic vancomycin-resistant enterococci ("VRE") and methods thereof.

2. Description of the Related Art

Vancomycin-resistant enterococci (VRE) represent a serious problem for healthcare worldwide. Both vanA and vanB genes of enterococci have been found to be associated with the increased resistance. Transfer of the vanA and vanB antibiotic resistance genes to non-enterococcal species is also a growing concern. The vanA gene has been found in *Corynebacterium, Arcanobacterium* and *Lactococcus* species (Power et al., *J. Antimicrobiol. Chemother*. 36:595–606, 1995). Recently, Poyart et al. (*Antimicrobiol. Agents Chemotherap*. 41:24–29, 1997), reported an occurrence of a *Streptococcus bovis* clinical isolate with a VanB resistance phenotype. The gene was shown to be highly homologous to the prototype vanB gene from Enterococcus. Increased use of antibiotics has resulted in the emergence of vancomycin-resistant microorganisms, such as *Enterococcus* spp. and *Staphylococcus* spp. (Dutka-Malen et al., *Antimicrobiol. Agents Chemother*. 34:1875–1879, 1990).

Briefly, there are four phenotypes of enterococci that can be separated based on expression of constitutive and inducible resistance of the glycopeptides, vancomycin and teicoplanin (Leclercq and Courvalin, *Clin. Infect. Dis*. 24:545–556, 1997). Inducible resistance to high levels of vancomycin (MIC≧64 mg/l) and teicoplanin (MIC≧16 mg/l) is characteristic of the VanA phenotype. This type of resistance is plasmid mediated. The vanA gene has recently been found on mobile elements that can direct their own transfer from the chromosome of one *Enterococcus* strain to another. The VanB phenotype is described as inducible resistant to vancomycin with MIC of 4 mg/l to ≧1,000 mg/l but displaying susceptibility to teicoplanin. The vanB gene is transferable by conjugation in certain strains. The genes in the VanG phenotype produce constitutive resistance and occur in *E. gallinarum* and *E. casseliflavis* and *E. flavenscens* (Leclercq and Courvalin, supra; Navarro & Courvalin, *Antimicrobiol. Agents Chemother.* 38:1788–1793, 1994). Recently, a VanD phenotype has been reported and is characterized by moderate levels of vancomycin resistance and low level resistance to teicoplanin (cited in Leclercq and Courvalin, supra).

The majority of conventional methods for detection of glycopeptide resistant enterococci have drawbacks related to time, lack of specificity and sensitivity of detection. For example, detection of the glycopeptide resistant enterococci can be carried out by conventional susceptibility testing (broth and agar methods), but these techniques are slow, and automated detection is not recommended due to poor performance (Aarestrup et al., *Antimicrob. Agents Chemother*. 40:1938–1940, 1996).

Although the above methods can be used to detect VRE, there is an urgent need for a rapid and reliable method for simultaneously detecting the vanA gene and vanB genes from VRE, both in the hospital and community settings. The present invention provides compositions and methods for simultaneously and rapidly detecting the vanA and vanB genes. The present invention also provides other related advantages.

BRIEF SUMMARY OF THE INVENTION

Briefly stated, the present invention provides compositions and methods for simultaneously detecting vanA and vanB genes carried by *Enterococci*.

Within one aspect of the present invention, methods are provided for detecting the presence of a vancomycin-resistant microorganism in a sample, comprising: (a) contacting a sample that may have a target nucleic acid molecule with a nucleic acid probe and a cleaving agent, wherein the probe is substantially complementary to a portion of the target and comprises a nucleic acid molecule having the sequence of 5'-CATGATGTGTCGGTAAAATCTGCAATAGAGA-3' (SEQ ID NO:6); (b) incubating under conditions and for a time sufficient for the formation of a probe:target hybridized duplex and for the probe to be cleaved within the probe:target duplex; (c) recycling the target molecule at least once through step (b); and (d) determining whether at least one probe fragment is released from the complex, thereby detecting the presence of a vancomycin-resistant microorganism. In certain embodiments, the probe comprises a nucleic acid molecule having the sequence of 5'-CATGATGTGTCGG-TaaaaTCTGCAATAGAGA-3' (SEQ ID NO:5). In yet other embodiments, the cleaving agent is RNase H.

BRIEF DESCRIPTION OF THE SEVERAL VIEWS OF THE DRAWING(S)

FIG. 1 is a schematic illustration of one representative embodiment of a cycling probe reaction.

Figure 2:
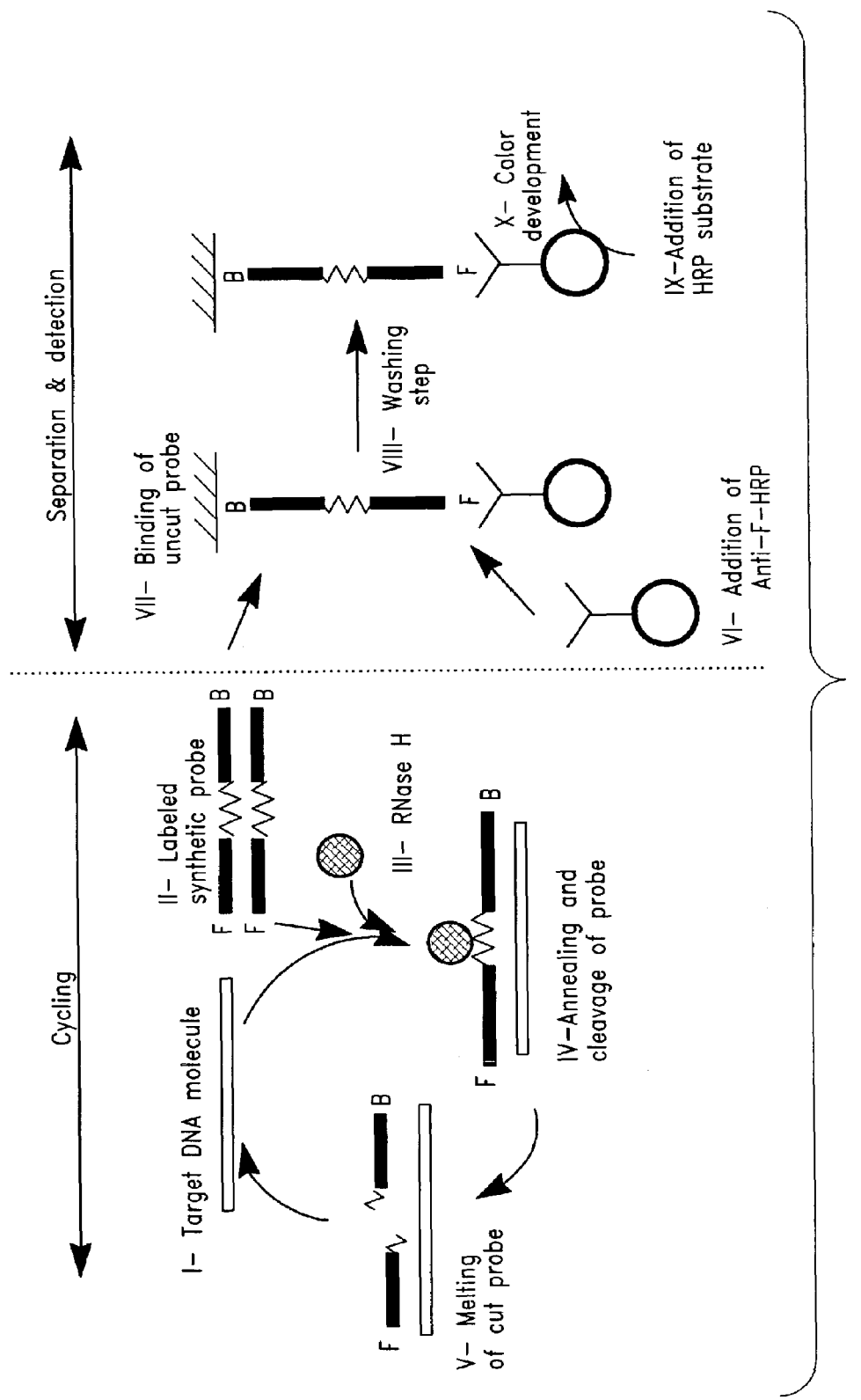

FIG. 2 is a schematic illustration of the one embodiment of a non-isotopic cycling probe reaction. Briefly, single-stranded target (I) serves as a catalyst for the cycling probe technology (CPT) reaction. In the presence of a fluoresceinated (F) and Biotinylated (B) DNA-RNA-DNA chimeric probe (F-DNA-RNA-DNA-B) (II) and RNase H (III), the RNA portion of the probe-target complex (IV) is cleaved by RNase H. The shorter cleaved probe fragments dissociate from the target thereby regenerating the target DNA for further cycling (V). The anti-fluorescein antibody coupled to horse radish peroxidase (anti-F-HRP) is added (VI) and the reaction is transferred to streptavidin coated plates. The uncut probe bound to anti-F-HRP is captured using the plates (VII). Excess antibody is washed away (VIII) and the HRP substrate is added (IX) to measure the amount of uncleaved probe. The absorbance, or color development (X), is inversely proportional to the amount of target DNA.

DETAILED DESCRIPTION OF THE INVENTION

Definitions

"Nucleic acid molecule" refers to a polymeric nucleotide or polynucleotide, which can have a natural or synthetic origin. Representative examples of nucleic acid molecules include DNA (ds- or ss-DNA), RNA, DNA-RNA hybrids, or nucleic acid molecules which are composed of or contain a nucleic acid analogue (e.g., α-enantiomeric forms of naturally-occurring nucleotides). Furthermore, nucleotides may be modified in their sugar moieties, or in the pyrimidine or purine base moieties. Examples of modification to sugar moities include modification or replacement of, for example, one or more hydroxyl groups with another group. Modifications to base moieties include alkyl or acylated pyrimidines and purines. In addition, nucleic acid monomers can be linked by phosphodiester bonds, or analogs of such linkages (e.g., phosphorothioate, phosphorodithioate, phosphoramidite, and the like).

"Isolated nucleic acid molecule" refers to a nucleic acid molecule that is not in its natural environment and/or is not integrated into the genomic DNA of an organism. Isolated nucleic acid molecules include, for example, probes and other synthetically or recombinantly generated nucleic acid molecules.

"Scissile linkage" refers to a nucleic acid molecule which is capable of being cleaved or disrupted without cleaving or disrupting any nucleic acid sequence of the molecule itself or of the target nucleic acid sequence. Scissile linkages include any connecting chemical structure which joins two nucleic acid sequences and which is capable of being selectively cleaved without cleavage of the nucleic acid sequences to which it is joined. The scissile linkage may be a single bond or a multiple unit sequence. An example of such a chemical structure is an RNA sequence. Other chemical structures suitable as a scissile linkage are a DNA sequence, an amino acid sequence, an abasic nucleotide sequence or an abasic nucleotide, or any carbohydrate polymer, i.e., cellulose or starch. When the scissile linkage is a nucleic acid sequence, it differs from the nucleic acid sequences of $NA_1$ and $NA_2$ (described below).

"Probe Containing a Scissile Linkage" refers to a synthetic nucleic acid molecule which is constructed in view of a known sequence to be complementary or substantially complementary to a target nucleic molecule. Within certain embodiments, the probe comprises the structure $[NA_1—S—NA_2]_n$, wherein $NA_1$ and $NA_2$ are different, non-complementary nucleic acid molecules and S is a scissile linkage, and n is an integer from 1 to 10.

"Ribonuclease H" ("RNase H") refers to an enzyme capable of specifically cleaving the RNA strand in RNA:DNA hybrid duplex (see, generally, Crouch & Dirksen in Nucleases, Linn & Roberts (Eds.), pp. 211–241, Cold Spring Harbour Laboratory Press, Plainview, N.Y., 1982).

"Universal base" refers to a base capable of pairing with each of the natural bases, adenine, guanine, cytosine and thymine in a duplex or alternatively it is not capable of pairing but does not destablize the opposite base in a duplex. Some examples of universal bases are inosine, indole, 5-nitroindole, 3-nitropyrrole and 5-nitropyrrole. A chimeric oligonucleotide probe can be synthesized to contain one or more universal base(s) at the appropriate position(s) matching mismatch(es) of one or more target sequences.

"Abasic nucleotide" or "Abasic site" refers to deoxyribonucleotide or ribonucleotide without the base portion. A chimeric oligonucleotide probe can be synthesized to contain abasic site at the appropriate position(s) matching mismatch(es) of one or more target sequences.

As noted above, the present invention provides a method for detecting the presence of a vancomycin-resistant microorganism in a sample, for example, comprising: (a) contacting a sample that may have a target nucleic acid molecule with a nucleic acid probe and a cleaving agent, wherein the probe is substantially complementary to a portion of the target and comprises a nucleic acid molecule having the sequence of 5'-CATGATGTGTCGGTAAAATCTG-CAATAGAGA-3' (SEQ ID NO:6) or 5'-CATGATGT-GTCGGTaaaaTCTGCAATAGAGA-3' (SEQ ID NO:5); (b) incubating under conditions and for a time sufficient for the formation of a probe:target hybridized duplex and for the probe to be cleaved within the probe:target duplex; (c) recycling the target molecule at least once through step (b); and (d) determining whether at least one probe fragment is released from the complex, thereby detecting the presence of a vancomycin-resistant microorganism. In certain preferred embodiments, the cleaving agent is RNase H.

Such methods may be utilized to detect the presence of a desired target nucleic acid molecule within a wide variety of biological samples. Representative examples of biological samples include clinical samples (e.g., blood, urine, stool, or abscess) and clinical samples grown and/or isolated on a bacteriological growth medium. Methods for generating target nucleic acid molecules may be readily accomplished by one of ordinary skill in the art given the disclosure provided herein (see generally, Sambrook et al., *Molecular Cloning: A Laboratory Manual* (2d ed.), Cold Spring Harbor Laboratory Press, 1989).

As noted above, within one aspect of the present invention the target nucleic acid molecule is reacted with a complementary single-stranded nucleic acid probe having a scissile linkage. Briefly, a wide variety of nucleic acid probes having scissile linkages may be utilized within the context of the present invention. Preferably, the probe is designed such that, upon cleavage by an enzyme which is capable of specifically cleaving the probe-target complex at the scissile link, probe portions are released which are detectable (see U.S. Pat. Nos. 4,876,187, 5,011,769 and 5,403,711). Preferred probe molecules of the present invention generally have the structure $[(NA_1)_x (—S—)_z (—NA_2)_y]_n$ wherein $NA_1$ and $NA_2$ are molecules composed of nucleic acids or nucleic acid analogues, —S— is a scissile linkage and x, y, and z are integers from 1–100 and n is an integer from 1–10. Within certain particularly preferred embodiments of the invention, $NA_1$ and $NA_2$ may range from 3 to 40 nucleotides, and when S is composed of nucleic acids, may range in size from 2 to 20 nucleotides. In addition, it should be understood that as utilized within the context of the present invention, each of x, y and z can vary with each iteration of n. Although within various embodiments of the invention a single-stranded probe is utilized to react or hybridize to a single-stranded target sequence, the above-described methods should not be limited to only situations wherein complementary probe and target sequences pair to form a duplex.

Within one embodiment, $NA_1$ and $NA_2$ as described above are DNA molecules which may or may not have the same sequence. Alternatively, $NA_1$ and $NA_2$ may be constructed of RNA molecules, which may or may not have the same sequence, or a combination of RNA and DNA molecules. The DNA or RNA molecules utilized may be derived from naturally occurring sources, or they may be synthetically formed. Each of $NA_1$ and $NA_2$ may be from about 5 bases to 10,000 bases in length.

Within other embodiments, $NA_1$ or $NA_2$ may be composed of nucleic acid analogues such as methyl phosphonates, carbamates, amidates, triesters, or "Peptide Nucleic Acids" ("PNA"). For example, PNA oligomers can hybridize to complementary target oligonucleotides (DNA or RNA) sequences with very high specificity. Such duplexes are more stable than the corresponding DNA-DNA or DNA- RNA duplexes (Egholm et al., *Nature* 365:556–568, 1993). Furthermore, PNA can bind to double stranded (ds) DNA by strand displacement (Nielsen et al., *Science* 254:1497–1500, 1991) and hence may obviate the traditional double strand denaturation requirement in sample preparation. Low concentration salt is generally preferred for binding of PNA to dsDNA ($\leqq$50 mM/L of Na$^+$). Moderate concentration of salt can inhibit binding through double strand displacement of PNA to dsDNA. However, once bound the PNA/DNA duplexes are stable to high concentration of salt. Further, these duplexes are also thermally stable compared to oligonucleotide/oligonucleotide duplexes (duplexes of PNA/DNA are more stable by approximately 1° C. per base pair compared to corresponding DNA/DNA). Based on the requirement of high sequence specificity to the target oligonucleotide, greater thermal stability and resistance to high salt concentration of the duplex once formed, PNAs are often ideal molecules for use in the methods described herein. Within certain embodiments, two short PNAs may be linked with scissile linkage and used as a highly sequence specific probe.

Single stranded nucleic acid molecules may be obtained and/or prepared directly from a target cell or organism utilizing standard techniques (see, e.g., Sambrook et al., "Molecular Cloning: A Laboratory Manual", Cold Spring Harbor, 1989), or prepared utilizing any of a wide variety of a techniques, including for example, PCR, NASBA, reverse transcription of RNA, SDA, branched-chain DNA and the like.

Probes of the present invention may also have one or more detectable markers attached to one or both ends (e.g., NA$_1$ or NA$_2$). The marker may be virtually any molecule or reagent which is capable of being detected, representative examples of which include radioisotopes or radiolabeled molecules, fluorescent molecules, fluorescent antibodies, enzymes, or chemiluminescent catalysts. Within certain embodiments of the invention, the probe may contain one or more labels such as a fluorescent or enzymatic label (e.g., quenched fluorescent pairs, or, a fluorescent label and an enzyme label), or a label and a binding-molecule such as biotin (e.g., the probe, either in its cleaved or uncleaved state, may be covalently or non-covalently bound to both a label and a binding molecule (see also, e.g., U.S. Pat. No. 5,731,146).

Within certain variants, the probe and target nucleic acid molecule need not be perfectly complementary, and indeed, may be purposely different by one, two, three or more nucleic acids (see, e.g., PCT Publication WO 95/14106 and U.S. Pat. No. 5,660,988). Within further variants, the target nucleic acid molecule is present in a heterogeneous population of genomic nucleic acids.

As noted above, the nucleic acid probe has a scissile linkage which is capable of being cleaved or disrupted without cleaving or disrupting any nucleic acid sequence of the molecule itself, or of the target nucleic acid sequence. As used within the context of the present invention, a scissile linkage is any connecting chemical structure which joins two nucleic acid sequences, and which is capable of being selectively cleaved without cleavage of the nucleic acid sequences to which it is joined. The scissile linkage may be a single bond or a multiple unit sequence. An example of such a chemical structure is an RNA molecule. Other chemical structures which may be suitable as a scissile linkage are DNA molecules, an amino acid sequence, an abasic nucleotide molecule or any carbohydrate polymer (e.g., cellulose or starch). When the scissile linkage is a nucleic acid molecule, it should differ from the nucleic acid sequence of NA$_1$ and NA$_2$.

In the nucleic acid probes described above, when n is greater than one, the unit NA$_1$—S—NA$_2$ repeats. As should be readily understood by one of ordinary skill in the art given the disclosure provided herein, the unit may be the same within each repeat, or may vary randomly in a defined pattern. In addition, the scissile linkage may also vary from unit to unit. For example, one scissile linkage may be an amino acid sequence, and another an RNA molecule.

As noted above, the probes of the present invention may also be linked to a solid support either directly, or through a chemical linker. Representative examples of solid supports include silicaceous, cellulosic, polymer-based, or plastic materials.

Within a particularly preferred embodiment of the invention, nucleic acid probes have the structure: [NA$_1$—S—NA$_2$]$_n$, wherein NA$_1$ and NA$_2$ are nucleic acid sequences, S is a scissile nucleic acid linkage, and n is an integer from 1 to 10. Within this embodiment, NA$_1$ and NA$_2$ are different nucleic acid sequences which are noncomplementary to each other, and —S— is a scissile linkage which is capable of being cleaved or disrupted without cleaving or disrupting NA$_1$ or NA$_2$, or a target nucleic acid sequence capable of hybridizing to the NA$_1$ or NA$_2$ sequences, wherein if the scissile linkage is a nucleic acid sequence it is RNA when both NA$_1$ and NA$_2$ are DNA sequences, or the scissile linkage is DNA when both NA$_1$ and NA$_2$ are RNA sequences.

Methods for constructing such nucleic acid probes may be readily accomplished by one of ordinary skill in the art, given the disclosure provided herein.

Nucleic acid molecules useful in the methods of the present invention can be constructed on a solid support medium (such as silica gel or controlled pore glass) using either a hydrolysable linkage or a permanent (non-hydrolysable) linkage. Published chemical methods were used for this synthesis. Oligonucleotide molecules are constructed as generally described by Matteucci and Caruthers, *J. Am. Chem. Soc.* 103:3185, 1981; Beaucage and Caruthers, *Tetrahedron Lett.* 22:1859, 1981; Alvarado-Urbina et al., "Automated Synthesis of Gene Fragments," *Science* 214: 270–274, 1981; see also U.S. Pat. Nos. 4,876,187, 5,011,769 and 5,403,711. For oligonucleotide analogs and conjugates synthesis see generally Agrawal (ed.) *Protocols For Oligonucleotides And Analogs, Synthesis; Synthesis and Properties*, Methods in Molecular Biology Volume 20, Humana Press Inc., 1993; Egholm et al., *Nature* 365:566–568, 1993; Dueholm et al., *J. Org. Chem.* 59:5767–5773, 1994; Agrawal (ed.) *Protocols For Oligonucleotide Conjugate, Synthesis And Analytical Techniques*, Methods in Molecular Biology Volume 26, Humana Press Inc., 1994. For non-isotopic probes see generally Kriscka, *Non-Isotopic DNA Probe Techniques*, Academic Press Inc., New York, 1992.

Particularly preferred probes (and synthetic targets) are based on the vanA, vanB, vanB2 genes published by Dutka-Malen et al., *Mol. Gen. Genet.* 224:364–372, 1990 (GenBank accession No. X56895), Evers et al., *Gene* 140: 97–102, 1994 (GenBank Accession No. U00456) and GenBank Accession No. Z83305 Gold et al. (*Antimicrobiol. Agents Chemother*. 37:1604–1609, 1993) has also published vanB2 sequence (GenBank Accession No. L15304). More preferred probes are single probes that are capable of simultaneously detecting any one of vanA, vanB or vanB2 genes, based on common sequences or modification such as use of abasic or universal nucleotides at mismatch positions in the sequences thereby allowing for the detection of these genes.

Briefly, oligonucleotide synthesis is accomplished in cycles wherein each cycle extends the oligonucleotide by one nucleotide. Each cycle consists of four steps: (1) deprotecting the 5'-terminus of the nucleotide or oligonucleotide on the solid support; (2) coupling the next nucleoside phosphoroamidite to the solid phase immobilized nucleotide; (3) capping the small percentage of the 5'-OH groups of the immobilized nucleotides which did not couple to the added phosphoramidite; and (4) oxidizing the oligonucleotide linkage to a phosphotriester linkage.

Representative methods for synthesizing oligonucleotides and biotinylation and fluoresceination of the oligonucleotides are described in Example 1.

Chimeric Probes for Detecting Multiple Vancomycin Resistance Genes

The vanA and vanB genes lack any significant homology and, therefore, it was not possible to find a common sequence that was suitable for use as a cycling probe technology (CPT) chimeric probe that is perfectly complementary to both vanA and vanB. Hence, a probe was designed to have two mismatches with the wild-type vanA gene in the 5' DNA arm and two mismatches with the wild-type vanB gene in the 3' DNA arm. In spite of the mismatches, the probe worked well to discriminate vanA and vanB from vanC and vancomycin-sensitive enterococci (VSE) isolates. In one preferred embodiment, the probe comprises vanB110-m3 (SEQ ID NO:5) and similar variants thereof.

In certain preferred embodiments, the probe may be further modified, for example, by altering the length of the probe, the type of nucleotide incorporated into the probe (e.g., using a chemically modified base as an abasic site), and by attaching different detection markers, as described herein.

Detection Reactions

As noted above, cycling reactions for the detection of a desired target nucleic acid molecule may be readily performed according to the general steps set forth above (see also, U.S. Pat. Nos. 5,011,769 and 5,403,711).

Other cycling reactions which may be performed include reacting a target nucleic acid molecule, a complementary single-stranded nucleic acid probe having a scissile linkage, under conditions which allow the probe to hybridize to the target nucleic acid and form a double-stranded, target-probe complex.

The compositions and methods provided herein may be utilized in a wide variety of other/related methods (e.g., U.S. Pat. Nos. 5,210,015; 5,487,972; 5,422,253; 5,691,142; 5,719,028; 5,130,238; 5,409,818; 5,554,517; 5,589,332; 5,399,491; 5,480,784; 5,215,899; 5,169,766; 5,194,370; 5,474,916; 5,698,400; 5,656,430; and PCT publication nos. WO 88/10215; WO 92/08800, WO 96/02668; WO 97/19193; WO 97/09444; WO 96/21144; WO 92/22671). Other variations of this assay include 'exponential' cycling reactions such as described in U.S. Pat. No. 5,403,711 (see also U.S. Pat. No. 5,747,255).

Representative examples of further suitable assay formats including any of the above assays which are carried out on solid supports such as dipsticks, magnetic beads, and the like (see generally U.S. Pat. Nos. 5,639,428; 5,635,362; 5,578,270; 5,547,861; 5,514,785; 5,457,027; 5,399,500; 5,369,036; 5,260,025; 5,208,143; 5,204,061; 5,188,937; 5,166,054; 5,139,934; 5,135,847; 5,093,231; 5,073,340; 4,962,024; 4,920,046; 4,904,583; 4,874,710; 4,865,997; 4,861,728; 4,855,240; and 4,847,194).

Within certain embodiments of the invention, cycling probe reactions may be performed utilizing additives such as polyamines (e.g., spermine) or ribosomal proteins which increase sensitivity, specificity, and/or rate of reaction. These, as well as other related aspects are described in U.S. Pat. No. 6,136,533 and WO 99/01570.

The following Examples are offered by way of illustration and not by way of limitation.

EXAMPLES

Example 1

Construction of Nucleic Acid Probes

Nucleic acid molecules can be synthesized utilizing standard chemistries on automated, solid-phase synthesizers such as PerSeptive Biosystems Expedite DNA synthesizer (Boston, Mass.), PE Applied Biosystems, Inc.'s Model 391 DNA Synthesizer (PCR-MATE EP) or PE Applied Biosystems, Inc.'s Model 394 DNA/RNA Synthesizer (Foster City, Calif.). Preferably, PerSeptive Biosystems Expedite DNA synthesizer is used and the manufacturer's modified protocol for making oligonucleotides is carried out.

Reagents for synthesis of oligonucleotides are commercially available from a variety of sources including synthesizer manufacturers such as PerSeptive Biosystems, PE Applied Biosystems Inc., Glen Research (Sterling, Va.) and Biogenex. For DNA and RNA synthesis, the preferred fluorescein amidite, phosphoramidites of deoxy-and ribonucleosides, 2'-O-methyl and reagents, such as activator, Cap A, Cap B, oxidizer, and trityl deblocking reagent are available from PerSeptive Biosystems. Biotin-TEG-phosphoramidite and Biotin-TEG-CPG are available from Glen Research. Ammonium hydroxide (28%) used for the deprotection of oligonucleotides is purchased from Aldrich. 1 M Tetrabutylammonium fluoride (TBAF) used for removing the 2'-O-tert-butyldimethylsilyl group is purchased from Aldrich and used after drying over molecular sieves for 24 hours. All buffers are prepared from autoclaved water and filtered through 0.2 µm filter.

The following procedure is used for preparing biotinylated and/or fluoresceinated oligonucleotides. Biotin-TEG-CPG (1 µmol) is packed into a synthesis column. Nucleoside phosphoramidites are then linked to make the defined nucleic acid sequence using PerSeptive Biosystem's modified protocol for making oligonucleotides. Fluorescein-amidite is dissolved in acetonitrile to a final concentration of 0.1 M. The fluorescein amidite is loaded on the synthesizer and added to the 5'- end of the oligonucleotide. Alternatively, phosphoramidite containing thio-linker is added at the 5'- terminal of the chimeric probe using the modified protocol. After the deprotection step described below, the probe is purified by reverse phase HPLC using Millipore's R-2 resin which retains the trityl containing oligonucleotide. In order to generate free reactive thio-group, the HPLC purified probe is treated with silver nitrate for 90 minutes at room temperature followed by neutralization of silver nitrate with dithiothreitol (DTT). The fluorescein-maleimide is then added to the free thio-group of the probe and then purified either by HPLC or by electrophoresis as described below.

After the synthesis of the oligonucleotide sequence, the resin bound oligonucleotide is treated initially with 25% ethanol-ammonium hydroxide (4 ml) at room temperature for 1 hour and subsequently at 55° C. for 16 hours in a closed tube. The tube is cooled, supernatant removed and concentrated to dryness in order to remove ammonia. The residue is dissolved in 1 ml of water and filtered through a 0.2 μm filter. The $OD_{260}$ is determined and an aliquot of approximately 2 $OD_{260}$ units is injected into the R-2 column of Biocad's HPLC to obtain a base line on the chromatogram for the tert-butyldimethylsilyl groups of the chimeric probe.

The remaining probe solution is lyophilized by centrifugal vacuum evaporator (Labconco) in a 1.5 ml microcentrifuge tube. The resulting oligonucleotide residue is deprotected with 1.0 M TBAF for 24 hours. To determine the extent of desilylation which has taken place, an aliquot of the TBAF reaction mixture is injected into the HPLC (R-2 column) using a linear gradient of 0 to 60% acetonitrile in 50 mM triethylammonium acetate (TEAA), pH 6.5. If only a partial desilylation has occurred, the TBAF reaction mixture is allowed to proceed for an additional 12 to 16 hours for complete removal of the protecting groups. The TBAF reaction mixture is quenched with 100 mM NaOAc, pH 5.5 and evaporated to dryness. The crude oligonucleotide product is desalted on a P-6 column (2 cm×10 cm, Bio-Rad), the fractions are concentrated to approximately 1 ml and the concentration measured at $OD_{260}$.

The crude oligonucleotide is purified by polyacrylamide gel electrophoresis (PAGE) using 20% polyacrylamide-7 M urea. The running gel buffer is 1×TBE (Tris-Borate-ethylenediamine tetraacetic acid (EDTA), pH 8.3 ) and the electrophoresis is carried out at 50 mA current for 3.5 to 4 hours. The oligonucleotide band is visualized with UV light, excised, placed in a 15 ml plastic conical tube and extracted by crushing and soaking the gel in 5 ml of 50 mM NaOAc (pH 5.5) for approximately 12 hours. The tubes are then centrifuged at 3000 RPM and the supernatant carefully removed with a Pasteur pipette. The gel is rinsed with 2 ml of the extraction buffer to remove any residual product. The combined extract is concentrated to a volume of approximately 1 ml and desalted on a P-6 column. The fractions containing the probe are pooled and concentrated to a final volume of approximately 2 ml. The analytical purity of oligonucleotides is checked by labeling the 5'- end of oligonucleotide with [γ$^{32}$P]-ATP and T4-polynucleotide kinase and then running the labeled oligonucleotide on PAGE. $OD_{260}$ is measured using Hewlett Packard's 845X UV spectrophotometer. The oligonucleotide solution is filtered through a 0.2 μm filter and stored at −20° C.

Utilizing the above procedures, the following exemplary oligomers were synthesized (upper case letters have been utilized to denote deoxyribonucleotides, and lower case letters have been utilized to denote ribonucleotides):

```
vanA with scissile link
                                  (SEQ ID NO:1)
5'-CAT GAC GTA TCG GTa aaa TCT GCA ATA GAG A-3' vanA
                                  (SEQ ID NO:2)
5'-CAT GAC GTA TCG GTA AAA TCT GCA ATA GAG A-3' vanB with scissile link
                                  (SEQ ID NO:3)
5'-CAT GAT GTG TCG GTa aaa TCC GCA ATA GAA A-3' vanB
                                  (SEQ ID NO:4)
5'-CAT GAT GTG TCG GTA AAA TCC GCA ATA GAA A-3' vanB110-m3 with scissile link
                                  (SEQ ID NO:5)
```

```
                      -continued
5'-CAT GAT GTG TCG GTa aaa TCT GCA ATA GAG A-3' vanB110-m3
                                  (SEQ ID NO:6)
5'-CAT GAT GTG TCG GTA AAA TCT GCA ATA GAG A-3'
```

Example 2

Preparation of Nucleic Acid Target Molecules from Bacterial Source

The following example describes the source of isolates, in house screening for enterococcal phenotypes, purification of genomic DNA from vancomycin resistant and sensitive isolates, and preparation of bacterial lysates.

1. Enterococcal Source

Vancomycin resistant and sensitive enterococcal (VRE and VSE) isolates were obtained from the following sites: 66 isolates from Mt. Sinai Hospital (Toronto, ON), 48 isolates from Wishard Memorial Hospital (Indianapolis, Ind.), 121 isolates from Cleveland Clinic Foundation (Cleveland, Ohio), 28 isolates from Vancouver General Hospital (Vancouver, BC), 143 isolates from Graduate Hospital (Philadelphia, Pa.), and 34 isolates from Royal University Hospital (Saskatoon, SK). There were approximately 440 enterococcal isolates available for screenings.

All isolates used in the following examples were tested with National NCCS Standardized antibiotic susceptibility testing with disc diffusion to vancomycin and teicoplanin, MIC to vancomycin and teicoplanin by E Test (AB Biodisc, Solna, Sweden) and assayed by VRE screening agar (PML Microbiological).

2. Purification of Genomic Enterococcal DNA

The following description is the procedure for purification of genomic DNA from VRE and VSE as essentially described generally by Marmur, *Meth. Enzymol.* 100:726–738, 1989). The isolates used for the purification were a vancomycin resistant VanA (IDB No. 339 obtained from Mt. Sinai Hospital), VanB *Enterococcus faecalis* (ATCC 51299, American Type Culture Collection, Rockville, Md.), and vancomycin sensitive *E. faecalis* (VSE, ATCC 29212) isolate. Enterococcal isolates for genomic preparation were grown overnight at 37° C. on 5% sheep blood trypticase soy agar (blood TSA) plates. A pre-culture is prepared by inoculating a single colony into 40 ml of Brain Heart Infusion (BHI) broth and grown for 6 to 8 hours at 37° C. This pre-culture is then added to a 1 liter of BHI broth and grown overnight at 37° C. with shaking. The cells are pelleted and washed once with 2% glucose, 1 mM ethylenediamine tetracetic acid (EDTA) and 10 mM Tris, pH 8.1 (TEG) buffer at 6800×g (Sorvall) for 5 minutes at 5° C. to 10° C. Lysis of cells is carried out by addition of 5 mg/ml of lysozyme (Sigma Chemical Company, St. Louis, Mo.) and incubation at 37° C. for 1 hr with shaking. Sodium dodecyl sulfate (SDS, 20%, electrophoretic grade) is added to a final concentration of 0.09%, and the suspension is mixed and incubated in a water bath at 50° C. to 60° C. for 10 minutes and held at room temperature for 1 hour. This is followed by addition of 24 ml of 5 M $NaClO_4$ and 40 ml of 25:24:1 of phenol:chloroform:isoamyl alcohol (v/v, PCIAA), and shaken for 2 hours at room temperature. The emulsion is aliquoted into sterile 30 ml glass tubes (Corex) and phase separation is carried out by centrifugation at 5000 rpm for 5 minutes in a table top Eppendorf centrifuge. The upper phase, containing the nucleic acid, is collected and precipitated by layering with 2 volumes of 95% ethanol. This is followed by spooling of the crude genomic DNA with a sterile glass rod, and resuspension in 40 ml of sterile 15 mM NaCl, 1.5 mM trisodium citrate (0.1×SSC) buffer. RNA is degraded by addition of RNase A solution (2 mg/ml, Pharmacia), to a final concentration of 50 μg/ml and RNase T1 (2500 units/ml, Gibco BRL Life Technologies, Gaithersburg, Md.) to a final concentration of 15 units/ml, to the crude DNA solution and incubating for 3 hours at 37° C. For removal of proteins, 2 ml of SDS (20%) and 2 ml of Proteinase K (5 mg/ml, Gibco BRL) are added and the solution is incubated at 50° C. for 5 minutes followed by 30 minutes at room temperature. The above PCIAA treatment is repeated with a 20 minutes mixing, followed by centrifugation, precipitation of the aqueous layer with ethanol, and spooling of DNA as described above, with the final resuspension in 10 ml of 0.1×SSC. The solution can be left overnight at 4° C. at this stage, or processing continued by addition of one ml of 10×SSC (to bring final concentration to 1×SSC), and 10 ml of chloroform-isoamyl alcohol (24:1, v/v, CIAA) with shaking for 15 minutes. The solution is then aliquoted into glass tubes and centrifuged at 5000 rpm for 5 minutes for phase separation. The lower organic phase is removed and the aqueous phase with the interface is re-extracted as described above with CIAA until there is minimal protein at the interface. This is followed by removal of the aqueous layer, precipitation with ethanol, and DNA spooling as described previously. The DNA is resuspended in 5 ml of 0.01×SSC and can be stored overnight. The DNA is dialyzed with one buffer change against 0.01×SSC at 4° C. over a period of 4 hours, repeated once overnight, and then repeated once again for a further 4 hours. The amount of purified genomic DNA is determined by UV spectrophotometry and then sonicated (Branson, model 250/450) for 10 minutes to reduce the size of DNA to less than or equal to 1000 base pairs (bp).

3. Preparation of Enterococcal Crude Lysates

Enterococcal isolates for crude lysates are grown overnight at 37° C. on blood TSA plates and cells are collected with a 1 μl plastic loop (PML Microbiological, Richmond, BC, Canada). Cells (equivalent to ≅5×McFarland No. 4 or 3×10$^8$ cells/50 μl) are resuspended in 50 μl of lysis buffer composed of 0.05% Triton X-100 and 20 mM TES, pH 6.8. As an alternative, cells are resuspended in 2 ml of lysis buffer and then adjusted to standard McFarland no. 4 (equivalent to ≅6×10$^7$ cells/50 μl). A combination of lytic enzymes, achromopeptidase (Wako Bioproducts, Richmond, Va.) and mutanolysin (ICN Biomedicals, Aurora, Ohio), were added to a final concentration of 150 units/ml and 50 units/ml, respectively. Samples are mixed and incubated at 54–58° C. for 20–30 minutes.

Example 3

Preparation of Thermostable RNase H

The following example describes one suitable method for preparing thermostable RNase H from *Thermus thermophilus*.

The cloning of the thermostable gene and its expression is described in detail in WO 95/05480 and Bekkaoui et al., *BioTechniques* 20:240–248, 1996 based on the modification of the method by Kanaya & Itaya, *J. Biol. Chem.* 267: 10184–10192, 1992. Briefly, the *T. thermophilus* RNase H gene (Kanaya & Itaya, supra) is cloned by PCR into vector pT7-7 (pIDB9) and is subcloned into the vector pET11a (Novagen) resulting in the plasmid pIDB33. Plasmid pIDB33 is subsequently transformed into the bacterial strain BL21(DE3) (Novagen, Madison, Wis.). BL21(DE3) cells containing pIDB33 are grown at 37° C. in LB medium (Sambrook et al, 1990) containing 0.1 mg/ml ampicillin. When the culture is at an OD$_{600}$ of 0.6–0.8, IPTG is added to a final concentration of 0.5 mM and the cells are cultured for four more hours. RNase H is expressed in the inclusion bodies with the pIDB33 construct.

Cells are harvested by centrifugation at 3000×g for 15 minutes at 4° C. Cell pellets are resuspended at 1 g fresh weight in 5 ml of TE buffer (10 mM Tris, pH 7.4, 1 mM EDTA buffer). The cells are lysed on dry ice/ethanol bath using a sonicator (Branson, model 450) and centrifuged at 15,000×g for 30 minutes at 4° C. The pellet is resuspended in 7 M urea in TE buffer, pH 8.0 and incubated with stirring for 2 hours at 4° C. The resuspended cells are sonicated for 2 minutes on ice, followed by centrifugation at 12,000×g for 10 minutes and the supernatant is collected and dialyzed overnight against 1l of urea sodium acetate buffer (8 M urea, 20 mM sodium acetate, pH 5.5) with two changes. After a centrifugation for 20 minutes at 31,000×g, the clear protein supernatant solution (150 ml) is collected and mixed with approximately 25 ml of pre-swollen phosphocellulose (equilibrated 2×in column buffer, P11, Whatman International Ltd., Kent, UK) for 3 hours. The resulting slurry is washed twice with the urea sodium acetate buffer and poured into a column. The column is connected to an FPLC system (Pharmacia) and step washed twice with 140 mM and 210 mM NaCl in the urea sodium acetate buffer. The protein is then eluted using a 0.21 to 0.7 M NaCl linear gradient in the urea sodium acetate buffer. At the end of the salt gradient, the column is maintained at 0.7 M NaCl until all the protein is eluted. Fractions are analyzed by SDS-PAGE and those containing RNase H are pooled and desalted using a Sephadex G-25 column with buffer containing 150 mM NaCl in 20 mM sodium acetate, pH 5.5. The eluted protein fractions are pooled, concentrated with a Centriprep 10 filter (Amicon, Beverly, Mass.), and stored at −20° C. in glycerol storage buffer (40% glycerol, 150 mM NaCl and 20 mM sodium acetate, pH 5.5).

Example 4

Cycling Probe Reactions

Cycling probe technology (CPT) reaction and conditions are modified from a previously published method (WO 95/14106; Bekkaoui et al., *BioTechniques* 20(2): 240–248, 1996). The chimeric probe is 5' labeled with radioactive [$^{32}$P]-ATP (Sambrook et al., 1990) using T4 polynucleotide kinase (RTG; Pharmacia Biotech, Piscataway, N.J.). Unless otherwise specified, the labeled probe is purified from unincorporated [$^{32}$P]-ATP by G50 NICK column (Pharmacia) chromatography. 1000 cpm of labeled probe corresponds to 0.3 fmol of probe. Unless otherwise specified, the final cycling reaction mixture contains specified concentrations of chimeric probe, and synthetic or natural nucleic acid target, and specified concentration of spermine and EGTA as additives in N-tris[Hydroxymethyl]methyl-2-aminoethanesulfonic acid (TES, Sigma Chemical Co.) based cycling buffer (TES-CB) which has the following composition: 0.05% Triton X-100®, specified concentration of MgCl$_2$, 20 mM TES buffer, pH 6.8. Sample preparations, probes and targets compositions and concentrations, RNase H, test additives, heterologous DNA concentrations, and other assay details are described specifically in the following examples.

Unless otherwise specified, the CPT reactions are incubated for 30 minutes at specified temperature and then stopped by addition of urea loading buffer (10 M urea, 100 mM EDTA and 0.025% each of blue bromophenol and xylene cyanol) on ice. The reaction mixtures are then resolved by 7 M urea- 20% to 24% acrylamide/bisacrylamide (19:1) gel electrophoresis (SDS-PAGE) at 500 Volts, with water cooling. The gel is analyzed on a PhosphorImager™ utilizing IMAGEQUANT™ software (Molecular Dynamics, Sunnyvale, Calif.). The amount of cycled probe is estimated by integration of the areas of bands corresponding to intact and cleaved probe.

Unless otherwise stated, in a CPT reaction Percent Probe Cut is the total amount of cut probe relative to the total amount of the input probe (Equation No. 1).

Percent Probe Cut=(Probe Cut/Total input probe)×100    (1)

In a simple CPT system, the C1 background refers to the Percent Probe Cut in the reaction buffer without RNase H or homologous target present. C2 refers to Percent Probe Cut in the presence of RNase H but without homologous target (Equation No. 2).

C2=(Probe cut/Total input probe)×100    (2)

For complex CPT system, C3 refers to Percent Probe Cut in the sample (biological samples that contains extraneous components, such as heterologous DNA or proteins) in the absence of RNase H. C4 refers to Percent Probe Cut in the biological sample in the presence of RNase H, but in the absence of homologous target (Equation No. 3).

C4=(Probe cut/Total input probe)×100    (3)

Net Percent Probe Cut is the percent of probe cut due to homologous target and is calculated by subtracting the background C2 (simple system), or C4 (complex system) from the Percent Cut (Equations No. 4 or 5, respectively).

Net Percent Cut=Percent Cut−C2    (4)

Net Percent Cut=Percent Cut−C4    (5)

Signal to noise ratio (S:N) for CPT is defined as the ratio of the Percent Probe Cut in the presence of the homologous target to the C2 (simple system, Equation No. 6) or C4 (complex system, Equation No. 7)

S:N=Percent Cut/C2    (6)

S:N=Percent Cut/C4    (7)

Example 5

Detection of Synthetic VRE Target by CPT Reaction

The following example examines the effectiveness of vanA and vanB chimeric probes for the detection of the synthetic vanA and vanB target by CPT reaction, in a clean system. Chimeric probes are designed and tested in a CPT reaction for non-specific cleavage both in the absence of the homologous target and RNase H (C1), and in presence of RNase H and absence of the target (C2). The VRE chimeric probes and targets were synthesized as described in Example 1 and the probes labeled as described in Example 4. Purified T. thermophilus RNase H was produced as described in Example 3. The CPT reactions and analysis were carried out essentially as described in Example 4 except for the following: 0.3 fmol specified chimeric probe, 1×10$^{-4}$ pmol specified target, 0.1 μg RNase H, 4 mM MgCl$_2$, in a final reaction volume of 10 μl in TES-CB and a reaction temperature of 65° C.

Preliminary results show that the certain chimeric probes result in Net Percent Probe Cut ranging from 61% to 91% and, therefore, can be used for detecting their complementary synthetic targets.

Example 6

Detection of VRE by CPT Reaction Using Genomic DNA

The following example demonstrates that the additives spermine and EGTA improve the detection of VRE in a CPT reaction using purified genomic DNA. Chimeric probes were tested for simultaneous detection of the vanA and vanB genes in VRE. The VRE chimeric probes were synthesized as described in Example 1 and labeled as described in Example 4. The genomic DNA was prepared from the VanA VRE isolate (from Mt. Sinai Hospital), the VanB E. faecalis (ATCC No. 51299), and the VSE E. faecalis (ATCC No. 29212) described in Example 2. The purified T. thermophilus RNase H was produced as described in Example 3. The CPT reaction and analysis were carried out as described in Example 4 except for the following: 0.9 fmol of specified chimeric probe, 100–150 ng of genomic DNA, 1 μg RNase H, 4.0 mM MgCl$_2$, with or without 0.5 mM spermine, 1.0 mM EGTA, in TES-CB to a total volume of 30 μl.

For detecting the vanA and vanB genes, it was observed that in the absence of spermine and EGTA, the C4 background was greater and the signal to noise ratio was less than 2 to 3. This was in contrast to the CPT reaction containing the additives, spermine and EGTA, where the signal to noise ratio increased to approximately 5. Therefore, the presence of spermine and EGTA improves the CPT reaction, allowing for the detection of both vanA and vanB genes of VRE.

Example 7

Non-Isotopic VRE Screen Using Probe vanB110-m3

This following example describes a rapid single probe non-isotopic CPT assay for screening dual VRE genes (vanA and vanB) from Enterococcal isolates. The non-isotopic VRE assay, which combines CPT with an enzyme immunoassay (CPT-EIA), is schematically illustrated in FIG. 2. Because of the lack of homology between the vanA and vanB genes, it was not possible to find a common sequence that was suitable for a perfectly complementary CPT chimeric probe. It was necessary to design a probe that had two mismatches to vanA in the 5' DNA arm and two mismatches to vanB in the 3' DNA arm. In spite of the mismatches, the probe worked well to discriminate vanA and vanB from vanC and VSE isolates.

The dual detection single chimeric probe specific for detecting vanA and vanB genes are synthesized, fluoresceinated and biotinylated as described in Example 1. The purified thermostable RNase H is prepared as described in Example 3.

The sequence of the vanB110-m3 probe and its homology to the vanA and vanB genes is shown below. Lower case letters in the probe sequence represent RNA and upper case DNA. The underlined bases in the vanA and vanB target sequences shown below indicate the mismatches.

| | Sequence | |
|---|---|---|
| vanB110-m3 | 5'-CAT GAT GTG TCG GTa aaa TCT GCA ATA GAG A-3' | (SEQ ID NO:5) |
| VanA | 5'-CAT GA<u>C</u> GT<u>A</u> TCG GTa aaa TCT GCA ATA GAG A-3' | (SEQ ID NO:1) |
| VanB | 5'-CAT GAT GTG TCG GTa aaa TC<u>C</u> GCA ATA GA<u>A</u> A-3' | (SEQ ID NO:3) |

The sources of Enterococcal isolates and growth conditions are as described in Example 2.

Lysis

The cells are lysed by placing a 1-μL loopful of culture growth in 50 μL of Lysis Reagent. The composition of Lysis Reagent is as follows: 0.2 mg/ml lysozyme (Sigma), 0.025 mg/ml mutanolysin (ICN Biomedicals, Aurora, Ohio), 0.05% (v/v) Triton X-100, 100 mM Trehalose and 20 mM TES buffer, pH 6.8. The samples are incubated at 54° C. for 10 minutes after which 50 μL of Clarifying Reagent (0.175% SDS and 20 ppm ProClin) are added and incubated at 54° C. for an additional 10 minutes.

2. Cycling Conditions

The composition of Cycle Reagent is as follows: 10 fmol of vanB110 m3 probe/50 μL, 1.5 μg RNase H/50 μl, 0.594% Triton X-100, 4 mM MgCl$_2$, 5.5 μM EDTA, pH 8.0, 1.38 mM spermine, antibacterial agent (20 ppm ProClin), and lyophilization additives (100 mM Trehalose, 0.224% PVP, 2.2 μg/μl BSA) in 24 mM TES, pH 6.8. The crude lysate from step A is heated at 95° C. for 5 minutes to denature the chromosomal DNA and then transferred to 54° C. dry bath prior to carrying out the CPT reaction. In each denatured crude lysate, 50 μL of Cycle Reagent is added to give a final reaction volume of 150 μL. Cycling reaction is carried out at 54° C. for 30 minutes.

3. Detection

After cycling, 3 drops (~100 μL) of Cycle Stop Reagent containing sheep polyclonal antifluorescein-horseradish peroxidase (HRP) conjugate and 0.16% SDS in Peroxidase Stabilizing Buffer (DAKO, Mississauga, ON) is added to the cycling reaction. The stopped reaction is transferred to streptavidin coated wells (Boehringer Mannheim GmbH, Germany) and incubated for 10 minutes at room temperature. The liquid is discarded and the plate washed twice with Wash Buffer (137 mM NaCl, 2.7 mM KCl, 1.8 mM KH$_2$PO$_4$, 10.1 mM Na$_2$HPO$_4$, 0.5% Tween 20, 20 ppm ProClin, pH 7.3). Detection is carried out by addition of 200 μL of HRP substrate (Ultra Sensitive TMB, Moss, Md.) and color allowed to develop for 5 minutes at room temperature. Color development is stopped with four drops (~100 μL) of Detection Stop Reagent (750 mM Tris, pH8.7, 0.5% NaF, 0.25% SDS). The plate is read with a Vmax plate reader at OD$_{650}$.

A mini-screen for identifying the vanA and vanB genes from 27 enterococcal isolates was carried out according to the above protocol. The collection of isolates included 9 Vancomycin Sensitive (Van S), 9 VanA, 6 VanB, and 3 VanC. The screen results of the CPT-EIA VRE assay with the vanB110-m3 probe are summarized in Tables 1 and 2.

TABLE 1

Overall OD$_{650}$ distributions of VanA, VanB, VanC, and Van S isolates from all five operators.

| OD$_{650}$ | Van A | Van B | Van C | Van S |
|---|---|---|---|---|
| 0.039–0.055 | 33 | 14 | 0 | 0 |
| 0.056–0.065 | 11 | 10 | 0 | 0 |
| 0.066–0.075 | 1 | 3 | 0 | 0 |
| 0.076–0.085 | 0 | 1 | 0 | 0 |
| 0.086–0.095 | 0 | 1 | 0 | 0 |
| 0.096–0.105 | 0 | 0 | 0 | 0 |
| 0.106–0.120 | 0 | 0 | 0 | 0 |
| 0.121–0.135 | 0 | 0 | 0 | 0 |
| 0.136–0.150 | 0 | 0 | 0 | 1 |
| 0.151–0.165 | 0 | 0 | 0 | 0 |
| 0.166–0.180 | 0 | 0 | 0 | 1 |
| 0.181–0.195 | 0 | 0 | 2 | 0 |
| 0.196–0.225 | 0 | 1 | 2 | 10 |
| 0.226–0.250 | 0 | 0 | 2 | 10 |
| 0.251–0.300 | 0 | 0 | 6 | 17 |
| 0.301–0.350 | 0 | 0 | 3 | 6 |
| Total | 45 | 30 | 15 | 45 |

TABLE 2

Categorical Identification using the OD$_{650}$ threshold at 0.14.

| | Velogene Positive | Velogene Negative | Total |
|---|---|---|---|
| VanA/VanB | 74 | 1 | 75 |
| VanS/VanC | 0 | 60 | 60 |
| Total | 74 | 61 | 135 |

Using 0.14 OD$_{650}$ as the threshold, the sensitivity and specificity were determined to be 98.7% and 100% respectively. This vanB110-m3 probe correctly identified all 9 VanA and 5 VanB isolates except one VanB.

The above example demonstrates a successful screening of the vanA and vanB genes of VRE clinical isolates by CPT reactions using a single chimeric probe, vanB110-m3.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for detecting the presence of a VanA vancomycin-resistant microorganism, a VanB vancomycin-resistant microorganism, or a dual VanA and VanB vancomycin-resistant microorganism in a sample, said method comprising:
   (a) contacting a sample that may have a target nucleic acid molecule with a nucleic acid probe and a cleaving agent, wherein the probe is substantially complementary to a portion of the target and comprises a nucleic acid molecule having the sequence of 5'-CATGATGTGTCGGTAAAATCTGCAATAGAGA-3' (SEQ ID NO:6);
   (b) incubating under conditions and for a time sufficient for the formation of a probe:target hybridized duplex and for the probe to be cleaved within the probe:target duplex;
   (c) recycling the target molecule at least once through step (b); and
   (d) determining whether at least one probe fragment is released from the complex, thereby detecting the presence of a VanA vancomycin-resistant microorganism, a VanB vancomycin-resistant microorganism, or a dual VanA and VanB vancomycin-resistant microorganism.

2. The method of claim 1 wherein the probe comprises a nucleic acid molecule having the sequence of 5'-CATGATGTGTCGGTaaaaTCTGCAATAGAGA-3' (SEQ ID NO:5).

3. The method according to claim 1 or claim 2 wherein the cleaving agent is RNase H.

4. The method according to claim 1 wherein the VanA vancomycin-resistant microorganism is a Van A vancomycin-resistant enterococcus, the VanB vancomycin-resistant microorganism is a VanB vancomycin-resistant enterococcus, and the dual VanA and VanB vancomycin-resistant microorganism is a dual VanA and VanB vancomycin-resistant enterococcus.

* * * * *

SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: vanA probe with scissile link
<220> FEATURE:
<221> NAME/KEY: misc_RNA
<222> LOCATION: (15)...(18)

<400> SEQUENCE: 1
catgacgtat cggtaaaatc tgcaatagag a                                31

<210> SEQ ID NO 2
<211> LENGTH: 31
<212> TYPE: DNA
<213> ORGANISM: Artificial Sequence
<220> FEATURE:
<223> OTHER INFORMATION: vanA probe

<400> SEQUENCE: 2
catgacgtat cggtaaaatc tgcaatagag a                                31

<210> SEQ ID NO 3
<211> LENGTH: 31
<212> TYPE: DNA
<213> ORGANISM: Artificial Sequence
<220> FEATURE:
<223> OTHER INFORMATION: vanB probe with scissile link
<220> FEATURE:
<221> NAME/KEY: misc_RNA
<222> LOCATION: (15)...(18)

<400> SEQUENCE: 3
catgatgtgt cggtaaaatc cgcaatagaa a                                31

<210> SEQ ID NO 4
<211> LENGTH: 31
<212> TYPE: DNA
<213> ORGANISM: Artificial Sequence
<220> FEATURE:
<223> OTHER INFORMATION: vanB probe

<400> SEQUENCE: 4
catgatgtgt cggtaaaatc cgcaatagaa a                                31

<210> SEQ ID NO 5
<211> LENGTH: 31
<212> TYPE: DNA
<213> ORGANISM: Artificial Sequence
<220> FEATURE:
<223> OTHER INFORMATION: vanB110-m3 probe with scissile link
<220> FEATURE:
<221> NAME/KEY: misc_RNA
<222> LOCATION: (15)...(18)

<400> SEQUENCE: 5
catgatgtgt cggtaaaatc tgcaatagag a                                31

<210> SEQ ID NO 6
<211> LENGTH: 31
<212> TYPE: DNA
<213> ORGANISM: Artificial Sequence
<220> FEATURE:

```
<223> OTHER INFORMATION: vanB110-m3 probe

<400> SEQUENCE: 6
catgatgtgt cggtaaaatc tgcaatagag a                                              31
```